(12) United States Patent
Welsh et al.

(10) Patent No.: US 10,360,349 B2
(45) Date of Patent: Jul. 23, 2019

(54) PERSONALIZED MEDICINE SERVICE

(71) Applicant: MolecularMatch, Inc., Houston, TX (US)

(72) Inventors: James Welsh, Houston, TX (US); Nicholas Tackes, La Canada, CA (US); Ryan Smith, San Clemente, CA (US)

(*) Notice: Subject to any disclaimer, the term of this patent is extended or adjusted under 35 U.S.C. 154(b) by 546 days.

(21) Appl. No.: 14/924,040

(22) Filed: Oct. 27, 2015

(65) Prior Publication Data
US 2016/0117470 A1 Apr. 28, 2016

Related U.S. Application Data

(60) Provisional application No. 62/069,197, filed on Oct. 27, 2014.

(51) Int. Cl.
*G06F 19/00* (2018.01)
*G06F 16/9535* (2019.01)
*G16H 10/20* (2018.01)
*G16H 10/60* (2018.01)
*G16H 50/70* (2018.01)

(52) U.S. Cl.
CPC ...... *G06F 19/3456* (2013.01); *G06F 16/9535* (2019.01); *G06F 19/326* (2013.01); *G16H 10/20* (2018.01); *G16H 10/60* (2018.01); *G16H 50/70* (2018.01)

(58) Field of Classification Search
CPC ......... G16H 10/20; G16H 10/60; G16H 50/70
See application file for complete search history.

(56) References Cited

U.S. PATENT DOCUMENTS

| | | | | |
|---|---|---|---|---|
| 2002/0099570 | A1* | 7/2002 | Knight | G06F 19/324 705/2 |
| 2004/0078216 | A1* | 4/2004 | Toto | G16H 10/60 705/2 |
| 2008/0195600 | A1* | 8/2008 | Deakter | G06F 19/325 |
| 2009/0089098 | A1* | 4/2009 | Schoenberg | G06Q 50/22 705/3 |
| 2009/0228445 | A1* | 9/2009 | Gangal | G06F 17/30539 |
| 2011/0004588 | A1* | 1/2011 | Leitersdorf | G06F 17/30864 707/711 |
| 2013/0238359 | A1* | 9/2013 | Carter | G16H 10/40 705/3 |

OTHER PUBLICATIONS

Priya; et al., "A Semantic Web-based System for Mining Genetic Mutations in Cancer Clinical Trials", AMIA 2015 Joint Summits on Translational Science (Clinical Research Informatics), San Francisco, CA. 2015.
Reed; et al., "Metastatic Soft Tissue Sarcoma Chemotherapy: An Opportunity for Personalized Medicine", Cancer Control (Jul. 2011), 18(3):188-95.

* cited by examiner

*Primary Examiner* — Jonathan Durant

(57) ABSTRACT

A system includes a knowledgebase for inferring relationships between biological categories, such as patient conditions, drugs, medical groups, genes, and trials. The system also includes a search engine for flexibly querying the knowledgebase to access relevant categories of results, such as drugs and ongoing clinical trials. The system may be a cloud-based system.

20 Claims, 14 Drawing Sheets

FIG. 7

GENE — 420

| Priority 1 | Priority 2 | Priority 3 | Priority 0 |
|---|---|---|---|
| briefTitle | arm groups | secondary outcome | inferred from mutation |
| title | | inclusionCriteria | trial assoc. from drug |
| keywords | | | |
| conditions | | | |
| briefSummary (purpose) | | | |
| interventions | | | |
| primary outcomes | | | |

MUTATION — 418

| Priority 1 | Priority 2 | Priority 3 | Priority 0 |
|---|---|---|---|
| briefTitle | arm groups | secondary outcome | trial assoc. from drug |
| title | | inclusionCriteria | |
| keywords | | | |
| conditions | | | |
| briefSummary (purpose) | | | |
| interventions | | | |
| primary outcomes | | | |

CONDITION — 410

| Priority 1 | Priority 2 | Priority 3 | Priority 0 |
|---|---|---|---|
| briefTitle | | | |
| title | | | |
| keywords | | | |
| conditions | | | |

SITE — 412

| Priority 1 | Priority 2 | Priority 3 | Priority 0 |
|---|---|---|---|
| | | | Inferred from condition | note: manual priority changes can be made on any of these

*FIG. 10A*

PERSONALIZED MEDICINE SERVICE

CROSS-REFERENCE TO RELATED APPLICATIONS

This application claims the benefit of U.S. Provisional Application No. 62/069,197, filed Oct. 27, 2014, which is incorporated by reference in its entirety.

FIELD OF THE INVENTION

The present invention relates to systems and methods for delivering precision medicine information, including information as concerns drug treatment and clinical trials based on a user's disease condition and molecular and genetic information, to users, for instance via an electronic, web-based portal.

BACKGROUND

Many databases have been created that contain information about drugs, genes, and conditions, but because of the varying nomenclatures used for medical and biological terms and concepts, and the vast quantities of information involved, it is difficult for even a sophisticated oncologist (or other specialized practitioners) to use these databases to obtain complete information about available drugs and trials for conditions, or simply to be aware of new drug trials. The situation is even more challenging for a patient interested in researching potential treatment options.

For example, a practitioner may have a patient with breast cancer, and a biopsy may have indicated that the cancer is ER/PR-positive. While the practitioner may have been aware that tamoxifen may be an appropriate treatment, the practitioner may not also have considered anastrozole, which may also be effective in treatment of breast cancers that are also ER/PR positive. The practitioner may also be unaware of clinical trials testing alternative treatments for ER/PR positive breast cancer that may be enrolling participants to evaluate such treatments, and the patient may match the participant profile. It would be desirable for the practitioner to be able to enter a search for ER/PR-positive cancer using a variety of nomenclatures and gain access to information about drugs and trials that could be appropriate for the patient.

Accordingly, there is a need for systems that can synthesize information from disparate sources, and integrate this information in an intelligent way so that, for example, relevant information in a reference about a drug for treating a condition may be associated with second reference describing a trial currently testing that same drug, even if the drug is referred to using different nomenclature in the two references. There is additional need for systems that can relate information in various references based on biological or biochemical relationships, such as information pertaining to drugs falling within a particular class of drugs. Disclosed herein are embodiments of an invention that address those needs.

BRIEF DESCRIPTION OF THE DRAWINGS

The above and other aspects and advantages of the invention will become more apparent upon consideration of the following detailed description, taken in conjunction with the accompanying drawings, in which like reference characters refer to like parts throughout, and in which:

FIG. 7 shows two views of an exemplary user interface for interacting with a system in accordance with some embodiments of the invention;

FIG. 10A and FIG. 10B shows exemplary domain instance connections that may be extracted from a record of a data source in accordance with some embodiments of the invention;

DETAILED DESCRIPTION

Figure 1:
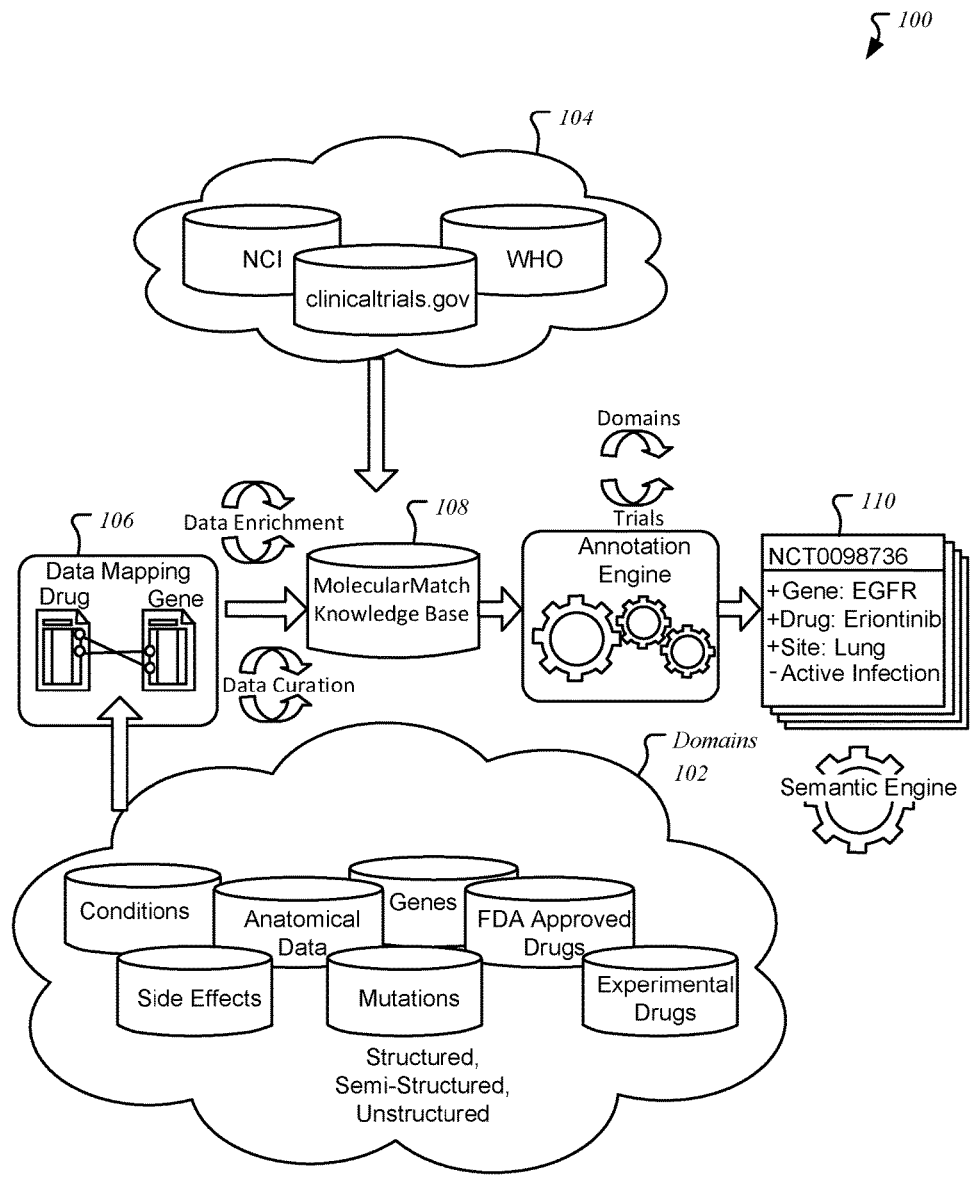
FIG. 1 is an exemplary system for inferring and delivering precision medicine information, in accordance with some embodiments of the invention.

Described herein are systems and methods for delivering precision medicine information, and, more particularly, such information as concerns drug treatment and clinical trials based on a user's disease condition and genetic information, to users for example via an electronic, web-based portal.

Embodiments of the present invention concern a system inferring and delivering precision medicine information: that is, a system for integrating information from disparate databases concerning—among other domains—drugs, genes, and conditions such that doctors and patients can search for a condition along with any other terms corresponding to domains that characterize the particular situation of a subject with the condition, and obtain all information about drug and drug trials relevant the subject's particular situation. In certain embodiments, the domain "genes" may also include mutation information, and in certain embodiments, "mutations" constitute a separate domain from "genes." The integration includes automatically inferring relationships between domains such as drugs, genes, and conditions based on biological or biochemical relationships (e.g., anatomical relationships, mutation and gene relationships, drug class-based relationships), and synonyms for terms. For instance, a drug trial and subject drugs pertaining to ER/PR-positive cancers will be automatically related to the genes ESR1 and PGR, both of which are implicated by the "ER/PR positive" mutation. Such relationships may be supported by publications, and this may inform any ultimate recommendations.

Each search result may be associated with a confidence measure that allows the user to view the most trusted drugs first, and that explains the strength of the evidence supporting the relevance of the drug or trial. Search results are assigned a higher confidence, where, for example, a drug is FDA-approved to treat a given condition, and assigned a lower confidence, where, for example, a trial examining a drug for treating a condition is in an early phase, such as Phases 1 or 2. Search results may additionally be provided alongside a confidence indicator for communicating the relevance or confidence in the particular result to a user.

The system also may incorporate manual integration of relationships and other information regarding domains including drugs, genes, and conditions, using scientific publications and expert annotations. For example, search results can be influenced by the user. A user can annotate a specific result (e.g., a specific drug pertaining to a mutation and diagnosis) with an affirmative or negative opinion that may be shared by or with subsequent recipients of a similar search. In certain embodiments, a user may augment a search to include additional results (e.g., a specific drug that applies to a diagnosis and mutation that was previously missing from the search results). Such an augmented result may be shared such that subsequent users may see the result included in the results for a similar search, and in certain embodiments subsequent users would see an annotation describing the user who provided the result and the reason for including it (e.g., user's name and institution). In certain embodiments, such annotations may be exposed as a shared annotation to everyone. In certain embodiments, such annotations may be exposed only to a particular organization or group affiliated with the annotating user (e.g., a diagnostic lab, a hospital, or an academic institution).

The system may be automatically updated using additions to the disparate databases. These automatic updates help enable the system to integrate a current summary of knowledge regarding drugs, genes, and conditions.

Further, practitioners and patients may use the system to obtain actionable information—a practitioner may use the system to identify prescribable drugs, and a patient may use the system to identify drug trials having compatible eligibility requirements. Prescribable drugs may be for on or off-label use. A pharmacy or insurer may use the system to evaluate the reasonableness of a proposed treatment for a condition.

Additionally, a patient wizard is provided that dynamically provides a series of questions that help to elicit information from a user for querying the system to identify the most relevant drugs and trials. The questions may be coordinated to elicit responses that will progressively expand and narrow the pool of drugs and drug trials that may be relevant to the patient's condition, until the patient is finally presented with the optimal set of results. Such a wizard can be useful for a naïve user (e.g., a patient or practitioner) who may be unaware of the range of types of relationships integrated into the system, or types of information that are useful for determining the applicability of a drug or trial to a patient's condition. As the user provides responses to the questions, the user is presented with a plain-language description of how the responses are used to build a query for the system.

FIG. 1 provides an exemplary system 100 for inferring and delivering precision medicine information. In some embodiments, the information delivered to a user is inclusive of drug treatment information and clinical trial information based on the user's disease condition and genetic information. The system may include five elements, which when combined constitute one embodiment of a system for delivering precision medicine information: (i) a knowledgebase 108, (ii) a curation platform for adding manual annotations to knowledgebase 108, (iii) means for processing and obtaining results using knowledgebase 108 (e.g., a "search engine"), (iv) means for allowing real-time updates to the knowledgebase 108, and (v) means for allowing a user to directly request enrollment in a trial. The knowledgebase 108 (also referred to as a knowledge graph) is a central data repository that is created by integrating multiple information sources, for example, public, online, biomedical information sources.

Figure 2:
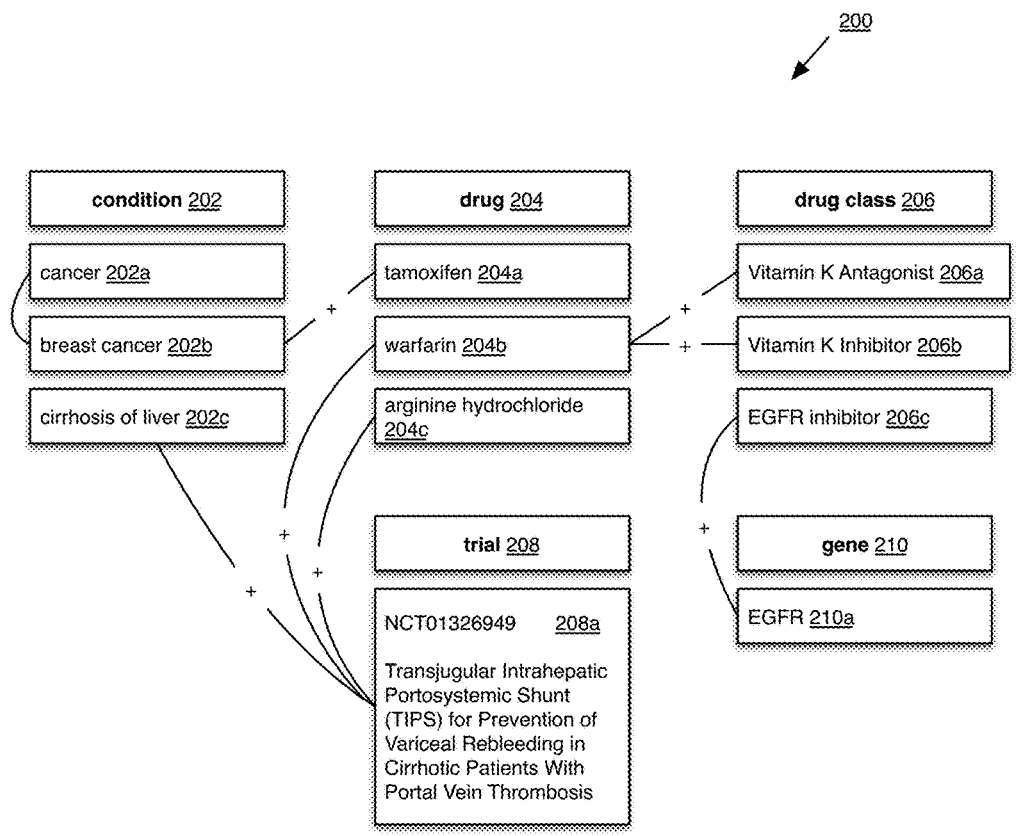
FIG. 2 is a diagram showing exemplary connections between exemplary database domain instances.
Figure 4:
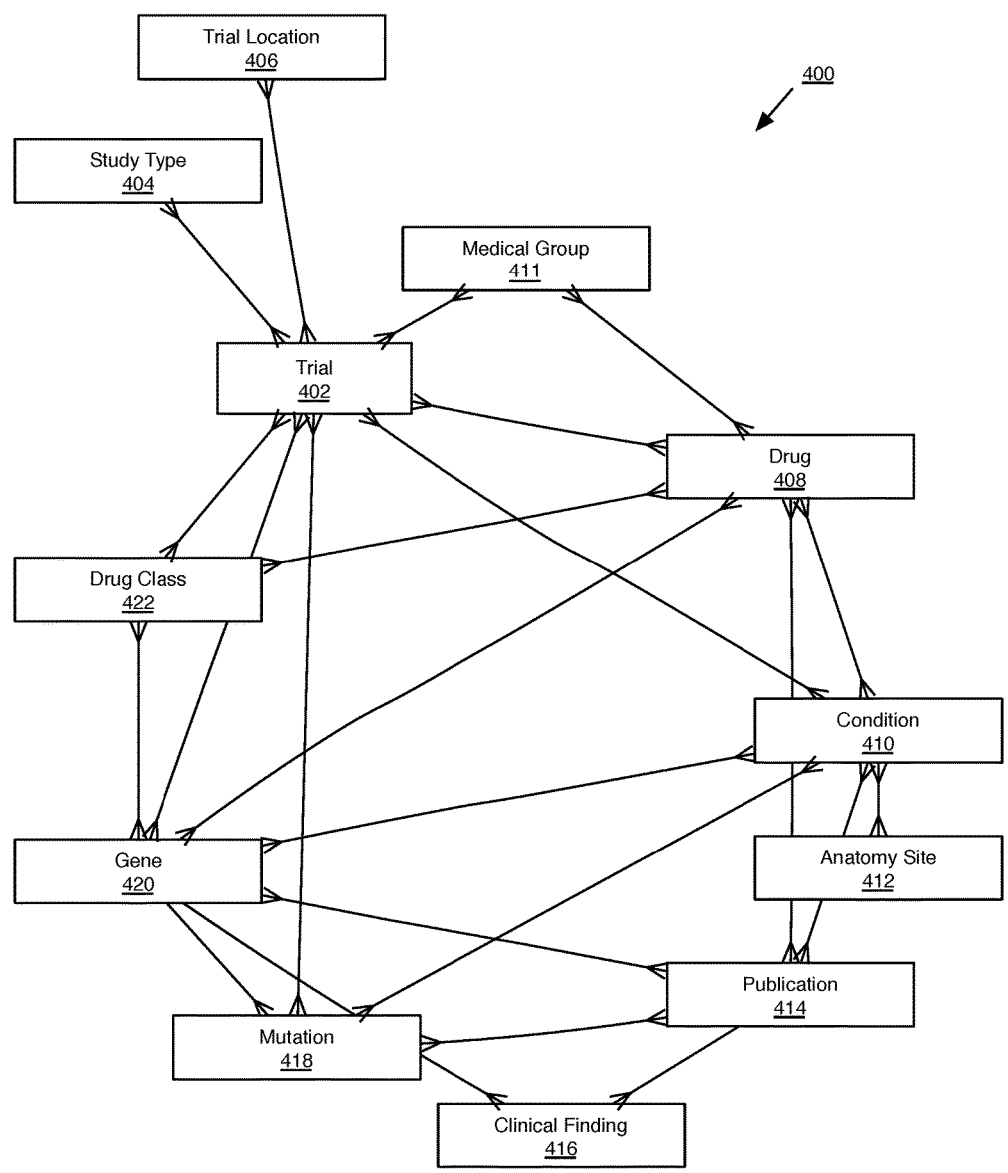
FIG. 4 is a diagram showing exemplary potential domain relationships, in accordance with some embodiments of the invention.

Domains 102 are categories of terms in the database, such as drugs, conditions, trials, and genes (which may include mutations and other molecular datapoints). FIG. 4 and its description provide more detail about exemplary domains 102 that may be included in a system, such as system 100. Each domain 102 is associated with one or more instances of the domain. FIG. 2 and its description provide more detail about how connections between instances can represent relationships between, for example, particular conditions, drugs, and trials. Instances may also be referred to as terms. Data mapping step 106 represents how domain instances may be connected to other domain instances in knowledgebase 108 to represent relationships between those respective instances. See, e.g., FIG. 2 and the related discussion for some examples, and FIG. 4 for exemplary types of domain instances and potential connections. Data sources 104 are sources of structured, semi-structured, and unstructured documents and data that include potential domain instances or terms, such as public, online, biomedical information sources. Knowledgebase 108 refers to one or more databases for storing and accessing domain relationships and corresponding direct and indirect connections between database domain instances falling within the same and different domains. Records 110 may refer to annotated source documents, and in some embodiments may refer to structured objects that represent all annotations/connections for a particular domain instance, such as a particular trial instance along with instances of other domain types that are associated with that particular trial. In some embodiments, annotations may be implemented via tags, or a particular drug instance along with instances of other domain types that are associated with that particular drug. For example, as shown in FIG. 1, exemplary record 110 represents trial NCT0098736, associated with gene: EGFR, drug: Erlotinib, and anatomical site: lung.

FIG. 2 is a diagram showing a subset 200 of connections between exemplary database domain instances that may be stored and accessed in knowledgebase 108. Subset 200 includes exemplary domains condition 202, drug 204, drug class 206, trial 208, and gene 210. Each domain in subset 200 includes one or more instances—for example, condition 202 shows three instances: cancer 202a, breast cancer 202b, and cirrhosis of liver 202c. Instances may be connected to other instances to as a representation of biologically or factually relevant relationships between those items. For example, breast cancer 202b may be connected to tamoxifen 204a, because tamoxifen is a drug for treating certain types of breast cancer. In another example, the trial 208a may be connected to drugs warfarin 204b and arginine hydrochloride 204c, because these drugs were administered in that trial, and cirrhosis of liver 202c, because the trial concerned that condition. Trial 208a may additionally be indirectly connected to Vitamin K Antagonist 206a and Vitamin Inhibitor 206b, as 206a and 206b are synonyms for a drug class 206 of which warfarin 204b is a member. In certain embodiments, trial 208a may be directly connected to drug classes 206a and 206b as inferred on the basis of trial 208a's administration of warfarin 204b. In another example, gene EGFR 210a is connected to the drug class EGFR inhibitor 206c, as members of this drug class target EGFR (Epidermal growth factor receptor). In some embodiments, instances within the same class may be connected through a parent-child or class-subclass relationship, such as parent cancer 202a and child breast cancer 202b. In some embodiments, instances may be connected because they are synonymous, such as drug classes 206a and 206b. In some embodiments, synonymous instances are resolved and treated as single instances.

The domain/instance relationships and connections of knowledgebase 108 may be stored using a key-value database, document-oriented database, object-oriented database, or other NoSQL database. In some embodiments, a relational database may be used. In some embodiments, a record 110 may be a document representing a certain domain instance, such as a trial instance (e.g., a trial object), and may represent connections to other instances using tags.

Figure 3:
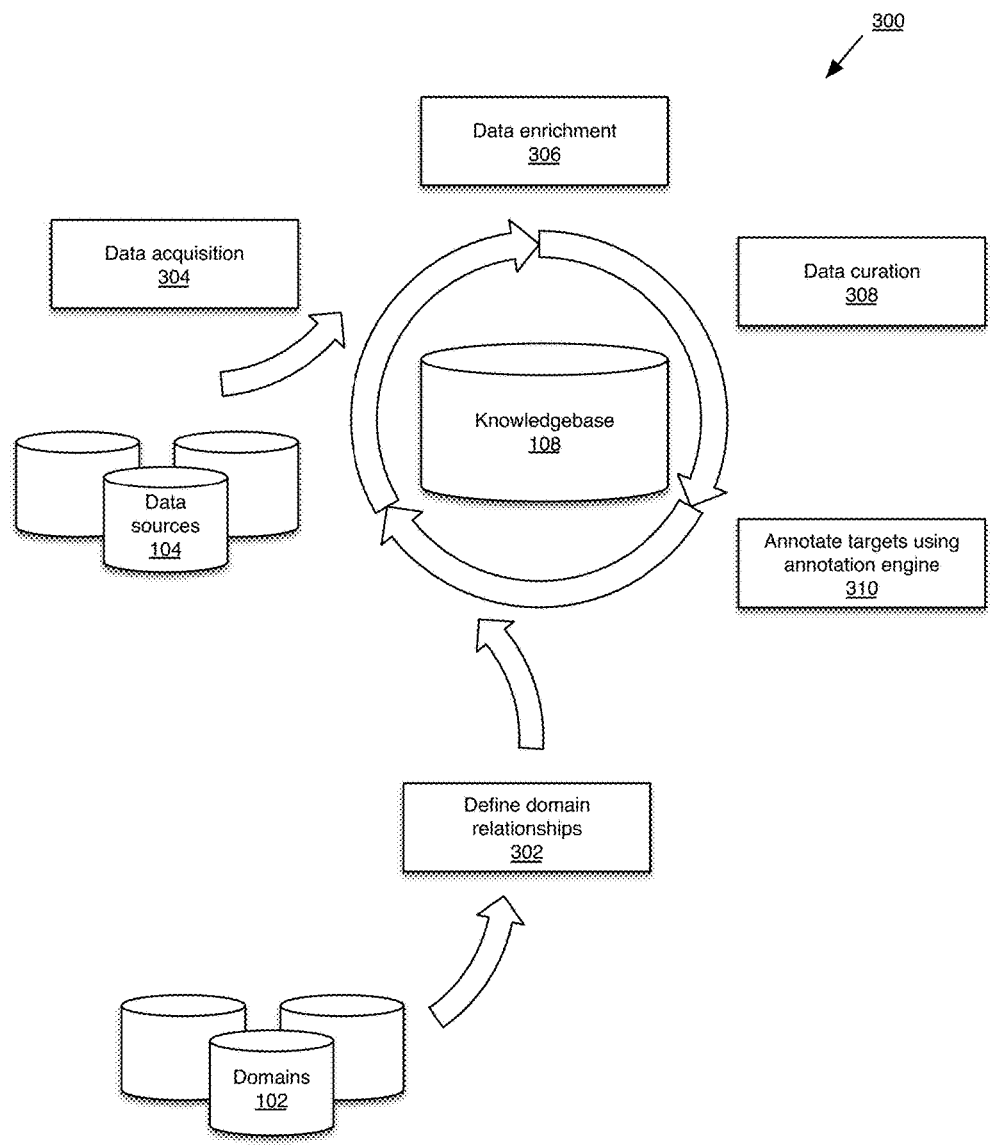
FIG. 3 is an exemplary system for inferring and delivering precision medicine information, in accordance with some embodiments of the invention.

FIG. 3 is an exemplary system 300 for inferring and delivering precision medicine information. Domains 102 are categories of terms in the database, such as drugs, conditions, trials, and genes. To build knowledgebase 108, domain relationships are defined (302)—for example, ontologies or medical vocabularies like the Systematized Nomenclature of Medicine (SNOMED) and the Unified Medical Language System, and gene nomenclature standards like Human Genome Organisation (HUGO) may be used to establish some of these relationships. These standards can provide frameworks for data annotation such as parent-child relationships between domain instances, synonyms, and condition/disease-anatomy relationships. The relationships may influence data tagging which influences the results returned to the user. This may be a manual process, an automated process, or a semi-automated process.

Data sources 104 are sources of structured, semi-structured, and unstructured documents and data that include potential domain instances or terms, such as public, online, biomedical information sources. These data sources are used to populate each domain with instances, such as trials, genes, mutations, conditions, clinical findings, drugs, and the like. Table 1 below lists exemplary domains and sources for those domains. Sources may include ClinicalTrials.gov (trials), National Center for Biotechnology Information (NCBI) EntrezGene (genes), NCBI PubMed (publications), and others. These data sources may provide a substantial portion of the overall data that make up the knowledgebase. The data may be acquired and organized into a relational database and later integrated into an ontological framework. This may be a manual process, an automated process, or a semi-automated process.

TABLE 1

Exemplary Sources of Domain Instances

| Domains: | Trials | Genes | Conditions |
| --- | --- | --- | --- |
| Sources: | ClinicalTrials.gov | NCBI EntrezGene | SNOMED |
| Domains: | Mutations | Drugs | Drug Classes |
| Sources: | cBioPortal (Cancer Genome Atlas) Catalog of Somatic Mutations in Cancer (COSMIC) | OpenFDA API Medkoo.com | OpenFDA API Medkoo.com |
| Domains: | Clinical Findings | Publications | Anatomy Sites |
| Sources: | SNOMED | NCBI PubMed Journal of Clinical Oncology | SNOMED |

During data acquisition process 304, the data are pulled from the data sources 104 in their native format (structured, semi-structured, or unstructured) and loaded into knowledgebase 108. During the acquisition process, the data may go through additional automated "scrubbing" processes including de-duplication and data normalization. The acquisition process is repeated regularly and augmented, creating metadata which is also stored with the data.

Data enrichment 306 refers to a process by which the data is transformed and augmented by processing it using a molecular and biomedical logic engine. This process connects the data into the knowledgebase in a specific fashion so that molecular and biomedical data elements/terms are appropriately mapped to the domains as instances. This allows the data to benefit from data inferences (e.g., a specific gene can infer a relationship with another gene) and parent-child relationships (e.g., non-small cell lung cancer is a child of lung cancer parent terminology). A rules engine is then utilized to execute performance-based instructions that allow for flexibility without updating the core code as well as a technical call-level interface that allows for integration with APIs.

In data curation process 308, subject matter experts may provide the latest scientific evidence and treatment options to provide additional augmented metadata. The knowledgebase may be manually curated by the subject matter experts, for example via a user interface that allows them to access information, change, enhance, delete, or add additional aspects to the data to make it more meaningful in terms of connectivity to various disease facts or markers.

In annotation step 310, additional domain instances are connected, for example, by "tagging" domain facts or classifications (e.g. "medical condition," or "gene," or "mutation"). The annotation process cycles through the array of domain facts. The resultant data from the transformation process is saved and may be referred to as "enriched data." This newly created data layer (or index) may become the backbone of the knowledgebase and the search engine is optimized to search against this data set.

Knowledgebase 108 may be queried as described in detail below. Such usage leads to improved quality as the system is used and reused (driven by analytics). For example, collaborative annotations may be evaluated for adoption into the knowledgebase 108. The knowledgebase 108 can be refreshed regularly (multiple times per day or week) to account for new biomedical discoveries and changes in the data sources.

FIG. 4 is a diagram showing a network 400 of exemplary potential connections representing relationships among domain instances. In certain embodiments, a knowledgebase 108 may include different domains than those described in FIG. 4—for example, it may include additional domains or fewer domains, or an overlapping set of domains, and may include connections that are not represented in FIG. 4.

An instance of trial 402 is a formal medical evaluation, such as a clinical trial. A study type 404 is a category of clinical trial. A trial location 406 is the location where a particular trial is based or administered from. A medical group 411 is an organization that may be associated with or responsible for a trial, drug, publication, clinical finding, or the like. A drug 408 is a therapeutic agent such as a molecule or macromolecule. A condition 410 is a disease or medical status that may be associated with a patient. An anatomy site 412 is a site in the human body that may be affected by a condition. A publication 414 is a public written work, such as an article describing research. A clinical finding 416 is a research observation, such as an association between a mutation 418 and a condition 410. A mutation 418 is a particular genetic variation, such as a specific single nucleotide polymorphism (SNP) in a gene 420. A gene 420 is a unit of genetic information that encodes a protein. A drug class 422 is a category of drugs 408, such as drugs targeting the same biological mechanism or signaling pathway, or drugs using the same chemical scaffold.

For example, an instance of trial 402 may be associated with a study type 404 such as "interventional" and a trial location 406 such as "Houston, Tex." and a medical group 411 such as "MD Anderson Cancer Center." The trial instance may concern evaluation of a drug 408 such as "Erlotinib hydrochloride" for treatment of a condition 410 such as "non-small cell lung cancer." Each of these instances may be connected to the trial instance in knowledgebase 108, for example as a tag in a trial document. As indicated by the connections in FIG. 4, each instance may by be connected to multiple instances of a domain—for example, a trial 402 instance may be associated with multiple centers and thus be linked to multiple trial locations 406. Non-small cell lung cancer may be connected to an anatomy site 412—e.g., "lung." The drug "Erlotinib hydrochloride" may be connected to the gene 420 EGFR and the mutations 418 "EGFR T790M" and "EGFR exon 19 deletion", as well as the manufacturer/medical group 410 "Genentech, Inc." and "Genentech Inc.".

Connections in knowledgebase 108 may indicate a positive relationship, such as the examples in the preceding paragraph. (E.g., the drug 408 "Erlotinib hydrochloride" is used for treatment of the condition 410 "non-small cell lung cancer.") Connections may also represent and be designated as a negative association or serve as exclusion factors: for example, if a particular trial 402 excluded patients with the condition 410 "neoplasm of colorectum" or patients taking drugs in the "anticoagulant" drug class 422, then these instances are associated to the trial with a negative connection.

Additionally, the knowledgebase 108 may account for synonyms by linking synonymous terms. Synonyms are related terms that include acronyms, alternate spellings, initialisms, and other terms with the same meaning. The knowledgebase 108 may also account for parent-child relationships. In certain embodiments, relationship between an instance and a parent may be attributed to the children of the parent term—for example, if a trial has a negative connection to the "anticoagulant" drug class 422, then the knowledgebase 108 may automatically infer that member drugs 408 of the "anticoagulant" drug class also have negative connections to the trial.

Figure 5:
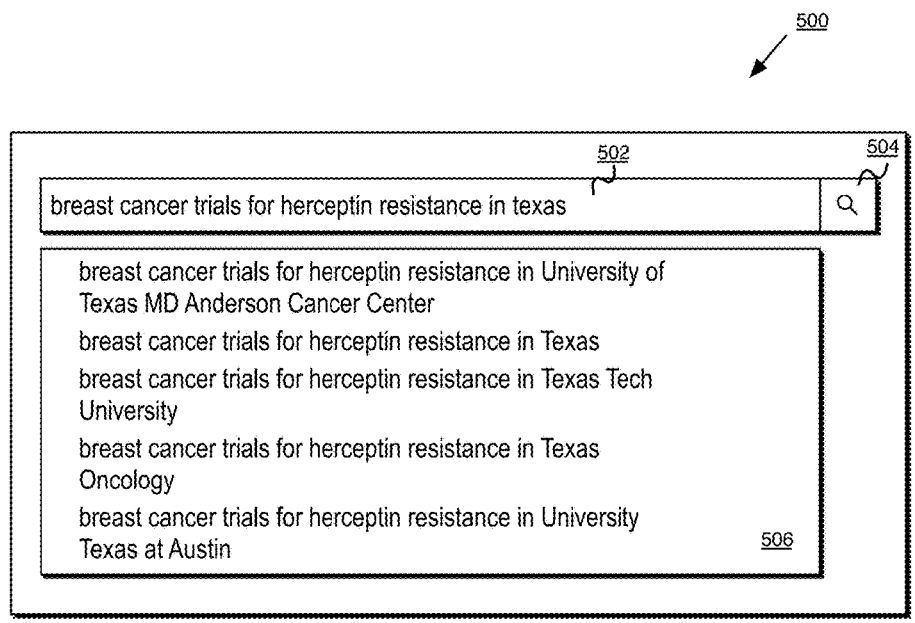
FIG. 5 is an exemplary user interface for querying a system in accordance with some embodiments of the invention.

FIG. 5 is an exemplary user interface 500 for querying an embodiment of knowledgebase 108. User interface 500 includes a search bar 502 for entering queries and a search button 504 for submitting queries concerning a patient's medical condition and/or status. The user may be the patient, or a user searching on behalf of a patient, such as a medical professional. In certain embodiments, user interface 500 may accept natural language queries. In certain embodiments, a query may require keywords. In certain embodiments, user interface 500 may provide search suggestions 506 based on a partially entered or to-be-submitted query. The search suggestions may be based on common terms seen in connection with some or all of the partially entered query. In certain embodiments, the search suggestions may represent search terms that correspond to search results, such as drugs and trials, that are available in knowledgebase 108. Such usage leads to improved quality as the system is used and reused (driven by analytics).

The knowledgebase 108 may be accessed via a free text omni-search bar. Any free text is transformed into a reference data model or "optimized query" in order to take advantage of the knowledgebase.

In certain embodiments, the system includes a query parser that extracts keywords from the user's query and formulates a database query for searching knowledgebase 108. Keywords may be used to search within domain instances, and/or may be used to search other structured, semi-structured, and unstructured data in knowledgebase 108.

Figure 6:
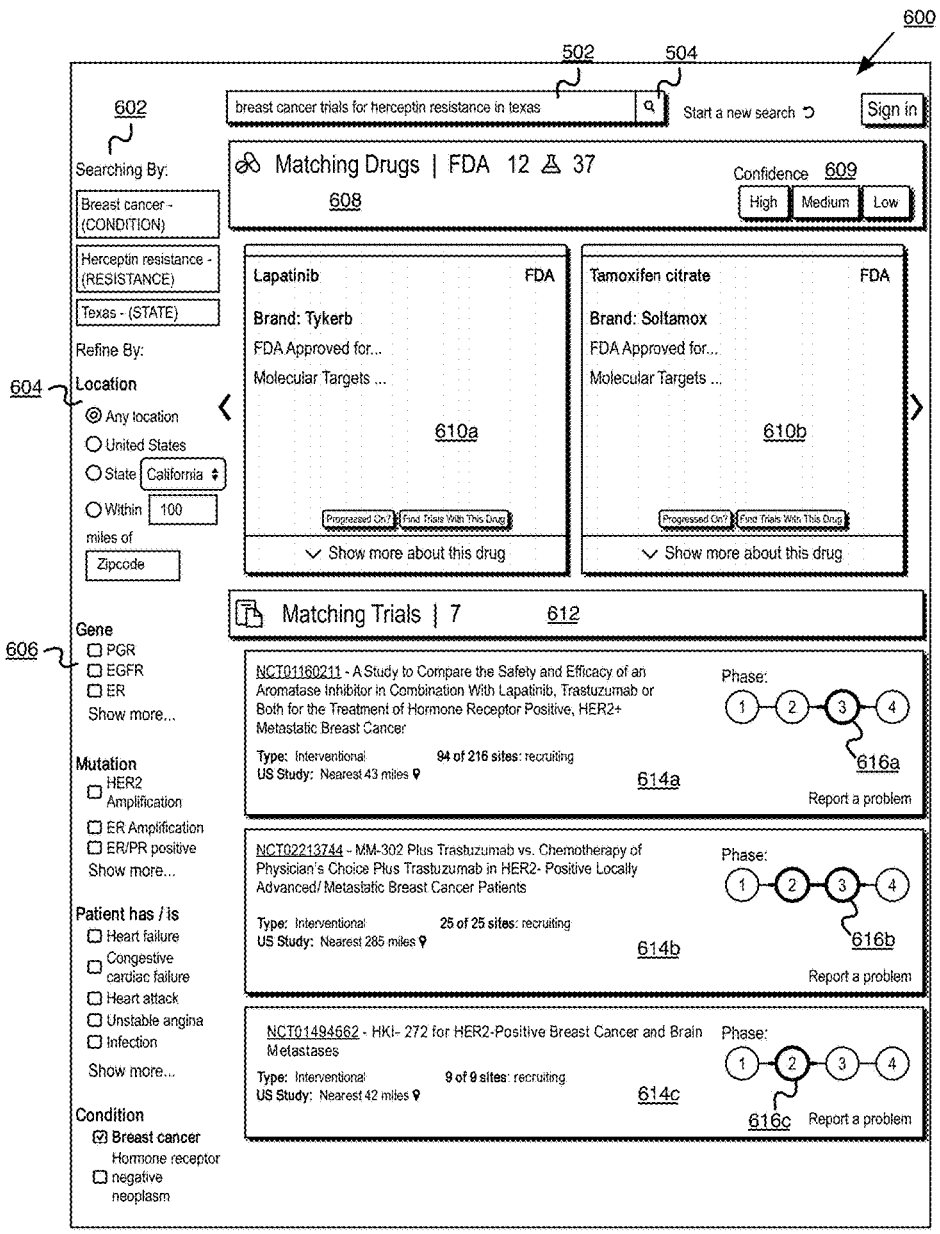
FIG. 6 is an exemplary user interface for interacting with a system in accordance with some embodiments of the invention.

FIG. 6 is an exemplary user interface 600 for interacting with an embodiment of knowledgebase 108. The personalized medicine information (targeted drugs and matching trial) results from the query may be presented to the user in a ranked fashion so that the best trials are at the top. User interface 600 includes a keyword filter 602 in which a user may view and modify the keywords extracted from the query entered into search bar 502. Also provided is a location filter 604, which will limit trial results based on an entered location and desired distance. Also provided is a domain instance filter 606, which provides selection of domain instances that may optimally limit or augment the search results based on a patient's status. The provided domain instances in filter 606 may be based on instances that are related to the current search results, and/or additional instances that are not present in the results but are available in the knowledgebase 108.

User interface 600 includes a matching drugs panel 608 and a matching trials panel 612. The results displayed in drugs panel 608 may correspond to instances of drugs 408, the results displayed in trials panel 612 may correspond to instances of trials 402. Drugs panel 608 includes a confidence legend 609 that provides an indication of the estimated relevance of each drug result to the database query. (For example, some aspect of the results displayed in drugs panel 608 may be colored according to confidence legend 610.) Drug results 610a and 610b display and provide access to more information about each drug, in addition to displaying a confidence indicator. In certain embodiments, such a confidence indicator corresponds to a confidence measure calculated for the drug instance as a candidate search result. In certain embodiments, such a confidence indicator reflects a different evaluation of the relevance of the drug. In certain embodiments, a confidence indicator is based on a confidence measure. In certain embodiments, the confidence indicator may indicate a qualitative assessment, or a status such as "FDA approved" or "experimental drug." Trials panel 612 displays trial results 614a, 614b, and 614c. Each trial result 614 displays information and links to more information about the respective trial. The trial phase indicators 616 display the current phase of the trial. In certain embodiments, only matching drugs or only matching trials may be provided.

Figure 7:
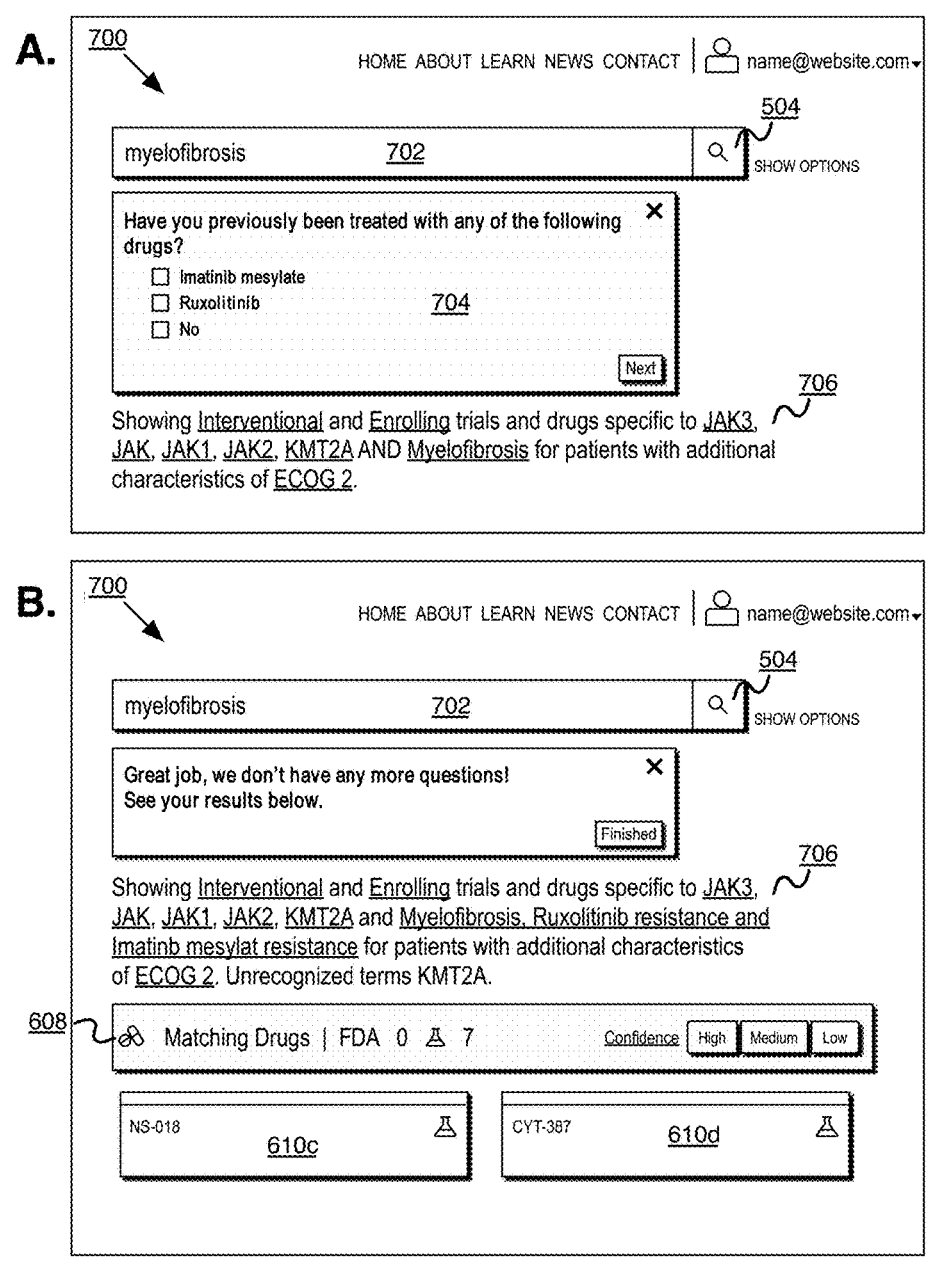

FIG. 7 shows two views of an exemplary user interface 700 for interacting with an embodiment of knowledgebase 108. This user interface 700 may be referred to as an interface for a patient wizard. FIG. 7A shows a search bar 702 where a user may enter an initial query, and a submit button 504. The system may pose a series of questions, where the first question is based on the initial query. The questions may request that the user select one or more domain instances or terms. The questions are posed to the user in dialog 704. As the user responds to each question, the user is provided with a description of a query 706 that is based on the user's initial query and responses to the questions. The query description 706 may use plain language and may convey which terms are used to exclude results, and which terms are used to augment results. FIG. 7B shows the user interface 700 after the user has answered all the questions, and a database query has been constructed based on the initial query and responses to the questions. After all the questions have been answered, the database query is submitted to knowledgebase 108, and results are provided to the user in the form of matching drugs panel 608 and matching trials panel 612. In certain embodiments, only matching drugs or only matching trials may be provided.

The user interfaces described above with respect to FIGS. 6-7 are exemplary. In some embodiments, these user interfaces may be provided via a web browser. In some embodiments, such user interfaces may take on a different form and/or be provided via enterprise software or another type of interface. In certain embodiments, a user may access the system directly via a command-line interface or a graphical user interface. See also the description in connection with FIG. 11.

Figure 8:
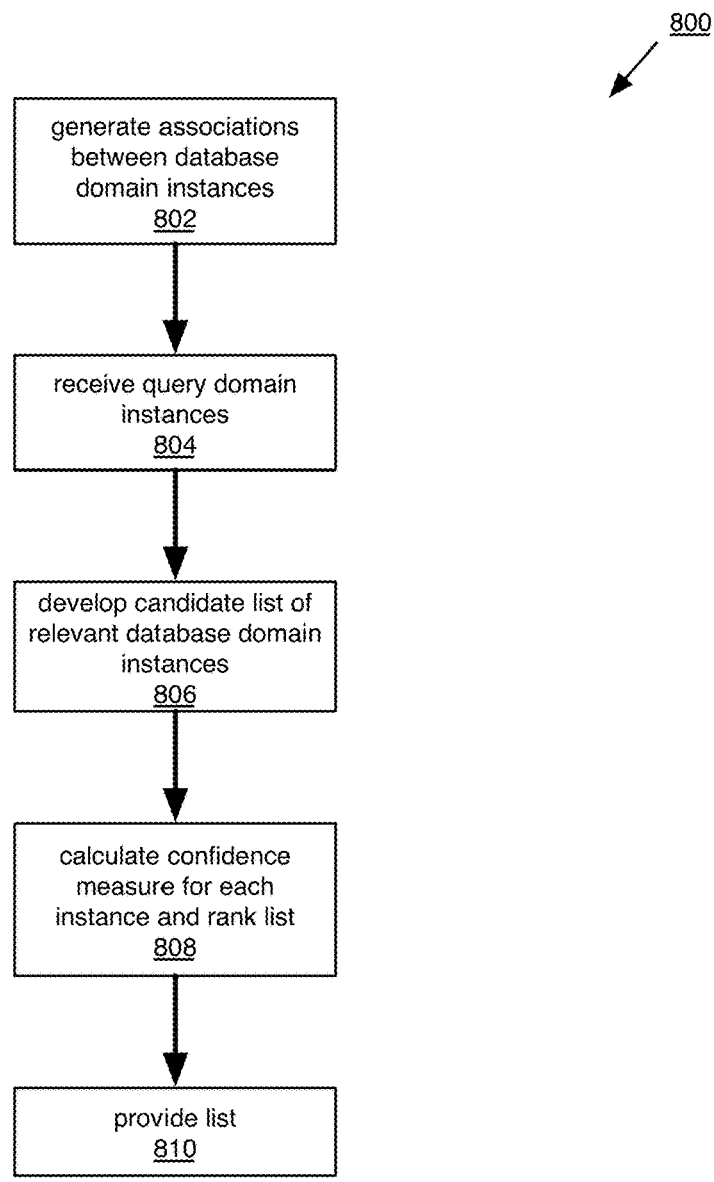
FIG. 8 is a flow chart depicting an exemplary process for handling queries to a system in accordance with some embodiments of the invention.

FIG. 8 is a flow chart depicting an exemplary process 800 for handling queries to an embodiment of knowledgebase 108. Before the system may be queried, the system must generate associations between database domain instances (802)—for example, knowledgebase 108 may automatically infer positive and negative connections between domain instances using the domain ontologies drawn from the definitions of domain relationships 302 and data sources 104. The system may update and generate associations at any time interval or in response to a particular request. In certain embodiments, the system updates and generates associations on a monthly, weekly, daily, hourly, or continuous basis.

Next, the system may receive query domain instances (804). The query domain instances may be received via a user interface such as 500, 600, or 700 and in certain embodiments by way of a query parser.

Next, the system may develop a candidate list of database domain instances that are potentially relevant to some or all of the query domain instances (806). In some embodiments, a candidate list may be assembled from all database domain instances that are directly and/or indirectly connected to the database domain instances that match one or more query domain instances in knowledgebase 108. In certain embodiments, matching domain instances includes finding identity between a query domain instance and a database domain instance. In certain embodiments, matching includes finding similarity between a query domain instance and a database domain instance, or a synonymous relationship. In some embodiments, the candidate list includes only drug instances and/or only trial instances. In some embodiments, the candidate list excludes instances that have a negative direct and/or indirect connection to a database domain instance that matches a query domain instance. Such negatively connected instances may constitute an exclusion factor. In certain embodiments, a candidate list may be assembled using query domain hits or matches to tags (representing database domain instances) in a document or object representing drug instances and/or trial instances.

Next, the system may calculate a confidence measure for each instance in the candidate list, and that measure may be used to rank the list or order the list (808). A description of calculating the confidence measure is discussed in detail below.

After the confidence measures have been calculated, the list of instances may be provided to a user by way of a user interface such as 600 or 700. In certain embodiments, some or all of the list may be provided prior to calculating a confidence measure for each instance. In certain embodiments, only instances associated with a confidence measure greater than or better than a desired/minimum confidence threshold are provided. In certain embodiments, the system may receive one or more filter parameters (for example, filters such as keyword filter 602, location filter 604, and domain instance filter 606), and may filter the instances using those parameters. In certain embodiments, such filter parameters may constitute exclusion factors when used to limit the list of instances.

Figure 9:
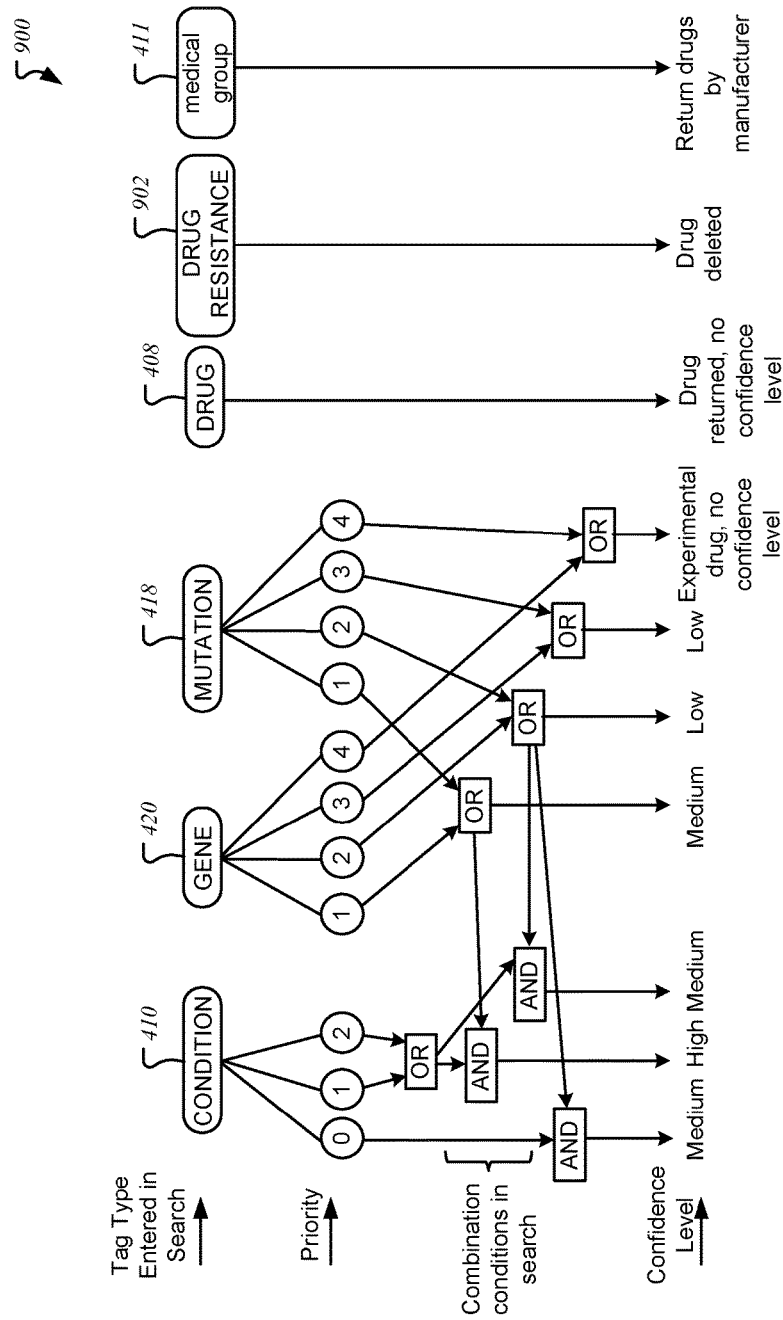
FIG. 9 is a diagram showing an exemplary approach for matching search queries to results and assigning a confidence level for results in accordance with some embodiments of the invention.

FIG. 9 is a diagram showing an exemplary approach for matching search queries to results and assigning a confidence level for results in an embodiment of knowledgebase 108. In certain embodiments, a confidence level may be a confidence measure used to rank and/or filter search results. In certain embodiments, drug 408 instances may have associated conditions 410, genes 420, mutations 418, drug resistances 902, and medical group 411 (i.e., manufacturer). Different actions may be taken on the drug search results based on the search input matching these associations. In certain embodiments, a confidence level of "high" is assigned to a drug instance in a candidate list of search results if the search input contained a priority 1 or 2 condition and a priority 1 gene or mutation. In certain embodiments, if just a priority 1 gene or mutation is matched, without a condition, the drug will receive a confidence of medium. In certain embodiments, when one or more drug instances are received as query instances, the search results only contain those drugs, and if a drug resistance term is entered, that drug is removed from the candidate list.

In certain embodiments, domain instances associated with drug instances produce different confidence scores when matched in the search based on their priority. The drug instance may have associated gene instances, mutation instances, and condition instances. These associations may have their priorities manually set based on FDA approval, prescription label information, and other drug information resources. In certain embodiments, in one example, a drug instance that is FDA-approved for a condition query instance would match a priority 1 condition and receive 35 points, and a drug instance that is experimental for a condition query instance would match a priority 5 condition and receive 7 points (See Table 2). Candidate drug instances may be ordered by their cumulative score. Experimental drugs may be ordered by their score, and by their trial phase and number of trials information. In certain examples, if multiple instances of a type are found in the same query, the scores are added together, less a constant factor; for example, where the constant factor is 40, if three gene instances appear in a query and a matching drug or trial, the score would be includeGENE1+includeGENE2−40+includeGENE3−40=70+(60−40)+(50−40)=100.

TABLE 2

Exemplary priority scores for calculating a confidence measure based on a query

| Priorities for Matched Terms In Query (Positive Associations) | Score |
| --- | --- |
| includeGENE0 | 50 |
| includeGENE1 | 70 |
| includeGENE2 | 60 |
| includeGENE3 | 50 |
| includeGENE4 | 20 |
| includeGENE5 | 10 |
| includeMUTATION0 | 15 |
| includeMUTATION1 | 25 |
| includeMUTATION2 | 20 |
| includeMUTATION3 | 15 |
| includeMUTATION4 | 10 |
| includeMUTATION5 | 5 |
| includeCONDITION0 | 3 |
| includeCONDITION1 | 4 |
| includeCONDITION2 | 5 |
| includeCONDITION3 | 3 |
| includeANATOMICALSITE0 | 5 |

In certain embodiments, priority assignments are used to differentiate the score of a hit or term matched to a query. For example, 'includeGENE1' is a type of tag on a trial; this tag is a gene and it has a priority of 1 (i.e., it may be an aspect of a connection relating a trial instance to a gene instance that assigns a priority level to the connection). Thus when a query term matches a gene that is an "includeGENE1" tag, 50 points are added to the confidence score of this result. In certain embodiments, a trial also has intrinsic priority assignment affecting its ranking in search results. This may be related to a trial's phase, enrolling status (enrolling—recruiting, available, enrolling by invitation; completed, etc), trial type (e.g., observational or interventional), or a custom score boost or reduction. Drug results may be ordered by their cumulative confidence score. Examples of intrinsic priority assignments (i.e., priorities that are not affected by the terms—including domain instances—present in the query) are provided below in Table 3. In certain embodiments, queries are formulated using conditional searches. There are some queries that may filter a candidate list for one of either tag/term/instance in a type (OR conditional), and some that filter the candidate list when all conditions of the type are matched (AND conditionals). Examples of conditional filters that may be used to filter results in the candidate list are provided below in table 4.

TABLE 3

Exemplary intrinsic priority scores for calculating a confidence measure

| Intrinsic Priorities for Trial Instances | Score |
| --- | --- |
| Phase 1 | 1 |
| Phase 1/2 | 4 |
| Phase 2 | 10 |
| Phase 2/3 | 13 |
| Phase 3 | 20 |

TABLE 3-continued

Exemplary intrinsic priority scores for calculating a confidence measure

| Intrinsic Priorities for Trial Instances | Score |
| --- | --- |
| Phase 3/4 | 23 |
| Phase 4 | 1 |
| Enrolling* | 1 |
| TrialType: Observational | −10 |
| Trialtype: custom | custom |

TABLE 4

Exemplary conditional filters

| Tag Type/Domain Type | Filter |
| --- | --- |
| Gene | OR |
| Mutation | OR |
| Phase | OR |
| Stage | OR |
| Status | OR |
| Trialtype | OR |
| Ecog | OR |
| Medicalgroup | OR |
| City | OR |
| State | OR |
| Country | OR |
| Drug | AND |
| Resistance | AND |
| Condition | AND |
| Finding | AND |
| Anatomical Site | AND |

Figure 10B:
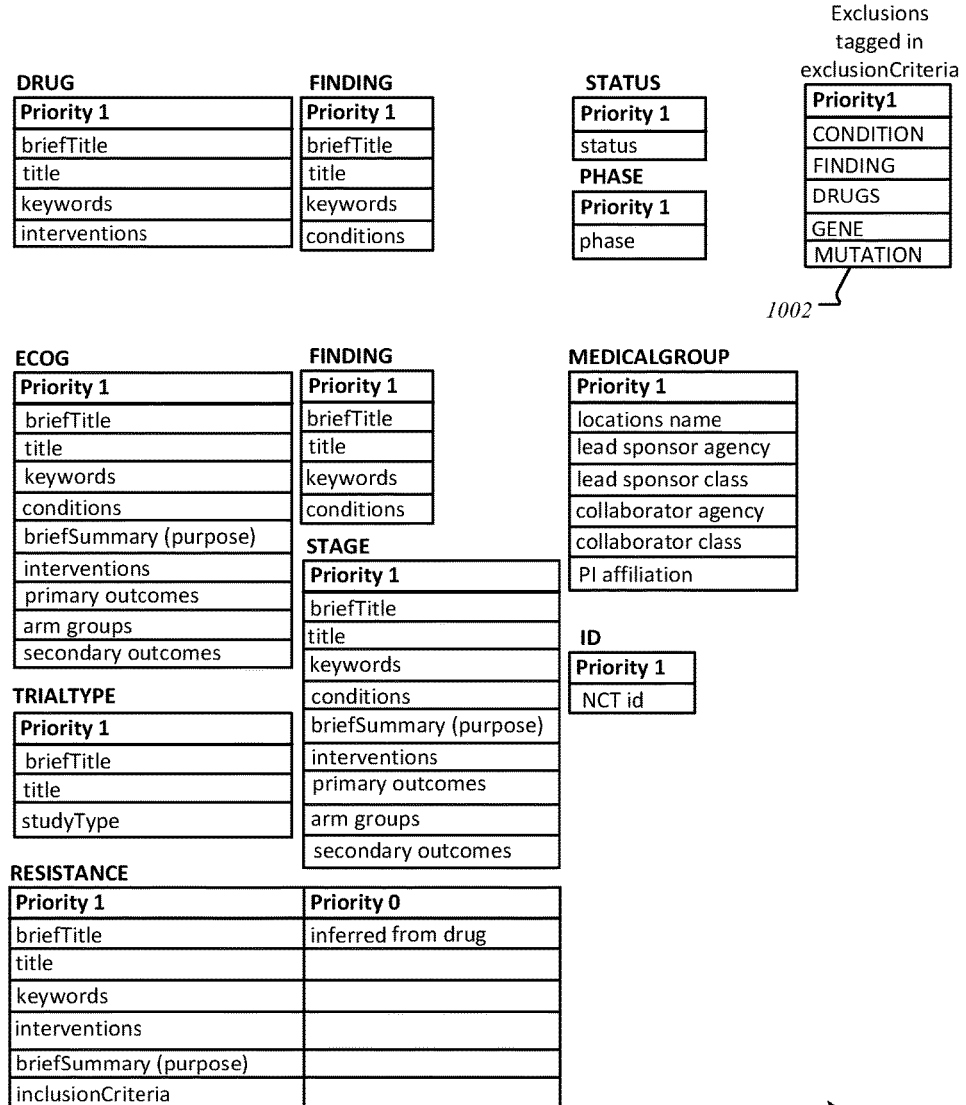

FIG. 10A and FIG. 10B shows exemplary domain instance connections 1000 that may be extracted from a trial document such as a trial object from clinicaltrials.gov (e.g., a record from one of data sources 104). Tag types (e.g., connected domain instances) may be assigned according to three items: their domain (e.g., gene, drug, mutation, etc.), their priority number, and their filter type (inclusion criteria versus exclusion criteria). The priority may be assigned to the tag type according to where in the trial the tag was found. In this example, the text of the trial object is searched to identify domain instances. A tag or domain instance connection (such as a gene 420 instance) may be associated with the trial instance corresponding to the trial described in the trial object depending on, for example, whether the gene 420 instance was found in a particular field of the trial object, or the gene 420 instance may be inferred based on the presence of another tag/instance such as a mutation 418 instance. More specifically, a gene 420 instance mentioned in a high priority, high confidence field of the trial, such as the title, keywords, conditions, primary outcomes, or interventions (e.g., the drug or procedure administered as part of the trial) for the trial object may be assigned a priority 1. A gene 420 found in an area of lesser confidence to the trial's intent (e.g., the secondary outcomes) may be automatically assigned a priority 3. In some embodiments, certain priority assignments are derived from tag objects themselves—for example, an anatomical site may be assigned a priority 0 and is inferred from a condition. A gene 420 may also be inferred based on the presence of a mutation 418 instance and assigned a priority 0. A negative tag/connection for a domain instance may be assigned based on finding the domain instance (e.g., condition, finding, drug, gene, mutation) in the trial object's "exclusionCriteria" field 1002—i.e., referring to reasons patients would be excluded from the trial described in the trial object.

A key feature of the knowledgebase is the ability to create and utilize inferred annotations (creating new information from existing information—e.g., automatically generating additional domain instances from a first domain instance, and creating connections from the first domain instance to the additional domain instances) (e.g. during the process of data enrichment 306). One specific example includes the ability to acquire information of a clinical trial 402 referencing a specific drug 408, such as Crizotinib that acts as an inhibitor of anaplastic lymphoma kinase (ALK) (a gene 420) in lung cancer (a condition 410) patients. Crizontinib also acts as an inhibitor of the c-ros oncogene (another gene 420). The unique aspects of the curation and annotation functions within the database allow for biology to be accounted for. Thus, users will be able to find information on drugs, treatments and trials with both an inference of ALK or c-ros, even if the original data source did not contain this inference or connection. In other words, the knowledgebase is molecular aware. Another example would be to understand that a patient is searching for information regarding lung cancer. The inferred connections allow the system to provide information related to lung cancer as well as clinical trial information for general "solid tumors."

Figure 11:
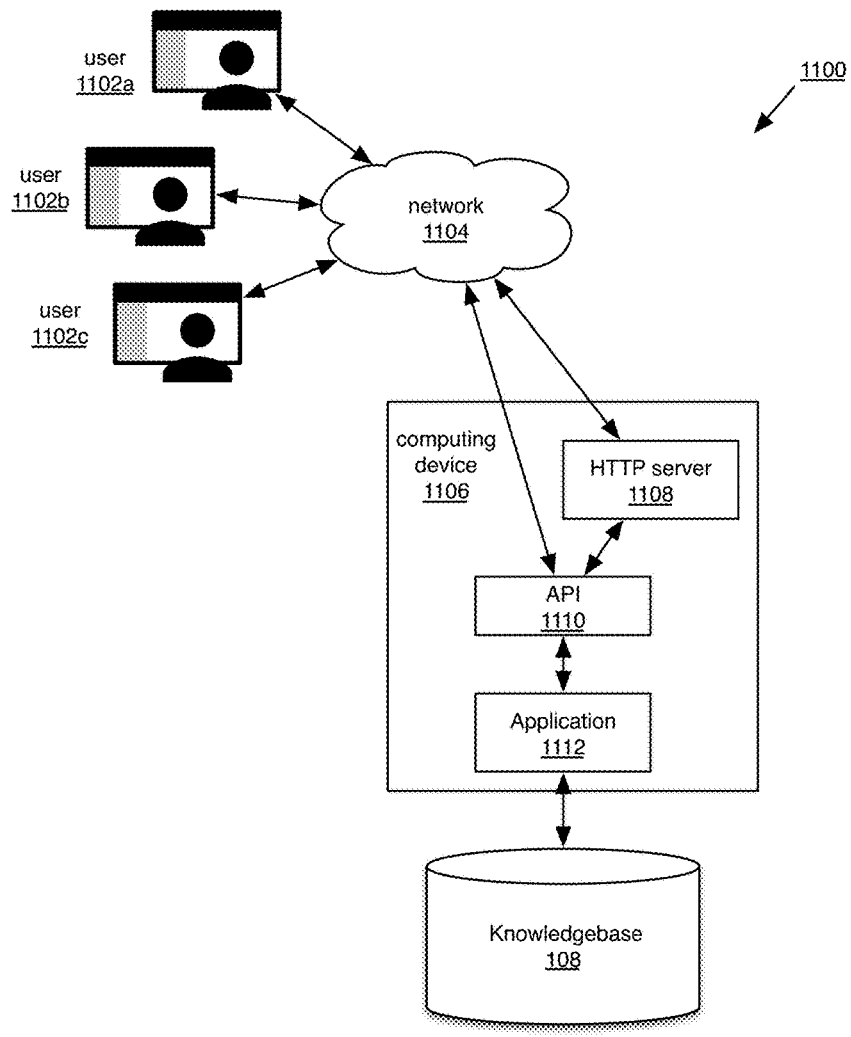
FIG. 11 is a block diagram showing exemplary data flows between users and the system in accordance with some embodiments of the invention.

FIG. 11 is a block diagram showing exemplary data flows between users 1102 and the knowledgebase 108 in exemplary system 1100. In certain embodiments, one or more computing devices 1006 host an HTTP server 1108 and application 1112 that provides access to knowledgebase 108. Application 1112 may support an Application Programming Interface (API) 1110 providing external access to methods for accessing knowledgebase 108. In certain embodiments, a user 1102 may access API 1110 directly via network 1104. Network 1104 may include a LAN, wired or wireless network, private or public network, or the internet. In certain embodiments, HTTP server 1108 may serve a user interface for querying knowledgebase 108 such as interfaces 500, 600, or 700. Users 1102 may access the user interfaces via computing devices including laptops, personal computers, smart phones, tablets, and the like.

In certain embodiments, a patient may receive pathology reports or other information regarding a biopsy, such as a tumor biopsy, indicating that the patient's tumor or condition is related to a particular one or more mutations. In certain embodiments, the the patient may receive information that could concern the patient's condition from an assay testing a sample from the patient, including florescent in situ hybridization (FISH), polymerase chain reaction (PCR), immunohistochemistry, arrays (array comparative genomic hybridization (aCGH), single nucleotide polymorphism (SNP) arrays, microarrays). In certain embodiments, the information concerning the patient's condition may be obtained using targeted panel sequencing, whole genome sequencing, or RNA sequencing. This information may be included as a keyword, term, and/or domain instance (e.g., a mutation or gene) in a query entered into, e.g., search bar 502 and used to search knowledgebase 108. In certain embodiments, such information may be used to query knowledgebase 108 directly via API 1110. In certain embodiments, the user may be a pharmacist, pathologist, insurer, or agent of an insurer.

In certain embodiments, the knowledgebase 108 may incorporate domain relationships (including relationships with drugs and trials) concerning cancers/oncology. In certain embodiments, knowledgebase 108 incorporates relationships concerning bone and mineral density disorders, behavioral disorders, neurocognitive and neurodegenerative disorders, cardiovascular disorders, and/or rheumatology.

In certain embodiments, synonyms and conceptual relationships characterizing domain relationships are represented in the knowledgebase 108. For example, a query including the medical group instance "MD Anderson" will retrieve hits to synonyms—e.g., the candidate list will include results (e.g., trials, drugs) that are connected to "MD Anderson", "M. D. Anderson", and "MD Anderson Cancer Center." A query including the medical group instance "U.S. Oncology" will retrieve hits to synonyms and subsidiaries including "US Oncology Network", "Rocky Mountain Cancer Centers", "Florida Cancer Affiliates", and "Arizona Oncology Associates". In another example, a user may seek drugs and trials concerning triple negative breast cancer. However, the condition "triple negative breast cancer" may be referred to in data sources using various phrasing and nomenclatures, including "ER−/PR−/HER2−", "Triple Negative or Luminal B/HER2 Normal BC", and ER−/PR− may be equivalent to "<1% stained cells", while HER2 negative may be equivalent to "IHC 0+, 1+ or IHC 2+". Such alternative phrasing concerning triple negative breast cancer may be represented in knowledgebase 108, for example, as tags.

In certain embodiments, search results may be presented in an actionable manner, for example, allowing users to identify relevant ongoing trials and request a patient's enrollment in those trials. For example, trial results 614 in trials panel 612 in user interface 600 may include links to request enrollment in a trial where the trial result 614 has a status of recruiting, available, and/or enrolling by invitation. In certain embodiments, selecting the link may allow the user to access a contact form. In certain embodiments, aspects of the contact form may be pre-populated based on information from the user's query and/or search results.

The present invention provides the ability for the knowledgebase to be updated via local data annotation. For example, subject matter experts, principal investigators, or trial administrators can update tags or specific data points for a particular trial and override the results of internal annotations. This includes trial inclusion and exclusion criteria, which are a critical part of the target profile and trial description. Moreover, negation text within the body of the trial identifying aspects of a patient's condition that would disqualify them from enrollment is utilized. in some examples, the annotation engine scores search results and provides prioritized information to the user. Drug concepts may have associated conditions, genes or mutations. Different actions are taken on the drug search results based on the search input matching these associations. Combinations of this matching also affects the action. For example, a confidence level of high is assigned to a drug in the search results if the search input contained a priority 1 or 2 condition and a priority 1 gene or mutation (see FIG. 9). If a priority 1 gene or mutation are matched, without a condition, the drug will receive a confidence of medium. When one or more drugs are entered into the search, the search results only contain those drugs. If a drug resistance is entered, that drug is removed from the results.

An algorithm is here, and generally, conceived to be a self-consistent sequence of steps leading to a desired result. These steps are those requiring physical manipulations of physical quantities. Usually, though not necessarily, these quantities may take the form of electrical or magnetic signals capable of being stored, transferred, combined, compared, displayed and otherwise manipulated. It proves convenient at times, principally for reasons of common usage, to refer to these signals as bits, values, elements, symbols, operations, messages, terms, numbers, or the like. It should be borne in mind, however, that all of these similar terms are to be associated with the appropriate physical quantities and are merely convenient labels applied to these quantities.

In the present invention, the operations referred to are machine operations. Useful machines for performing the operations of the present invention include digital computers or other similar devices. In all cases, the reader is advised to keep in mind the distinction between the method operations of operating a computer and the method of computation itself. The present invention relates to method steps for operating a computer, coupled to a series of networks, and processing electrical or other physical signals to generate other desired physical signals. The present invention also relates to apparatus for performing these operations. This apparatus may be specially constructed for the required purposes or it may comprise a digital computer selectively activated or reconfigured by a computer program stored in the computer. In such devices, a processor may control the overall functions of the digital computer such as running applications and controlling peripherals. Such a processor may communicate with an RF receiver and RF transmitter to transmit and receive wireless signals (e.g., via an antenna) such as cellular, Bluetooth, Wi-Fi, WiLAN, or other communication signals. The processor may use short-term memory to store operating instructions and to help in the execution of the operating instructions (e.g., such as the temporary storage of calculations and the like). The processor may also use non-transitory storage to store and read instructions (e.g., instructions that instantiate the methods of the invention), files, and other data that requires long term, non-volatile storage.

The processor may communicate and control other peripherals, such as a display with associated touch screen sensor, causing images to be displayed on the display and receiving input from the touch screen sensor when a user presses on the touch-screen display. In some examples, a touch screen sensor may be a multi-touch sensor capable of distinguishing and processing gestures.

The processor may receive input from a physical keyboard. In other examples, the device may utilize a touch screen keyboard using the display and touch screen sensor. The processor may produce audio output and other alerts that are played on a speaker. A microphone may be used as an input device for the processor to receive commands using voice-processing software.

An accelerometer may provide input on the motion of the device to the processor. An accelerometer may be used in motion sensitive applications, or, for example, in connection with scrolling content using tilting gestures, etc. A Bluetooth module may be used to communicate with Bluetooth-enabled external devices. A USB port may enable external connections to other devices (e.g., mice or other cursor control devices) supporting the USB standard and charging capabilities. An external storage module may include any form of removable physical storage media such as a flash drive, micro SD card, SD card, Memory Stick, and the like.

Certain embodiments are described herein as including logic or a number of components, modules, or mechanisms. Modules or components may constitute software modules (e.g., computer-executable instructions embodied on a non-transitory machine-readable medium) or hardware-implemented modules. A hardware-implemented module is a tangible unit capable of performing certain operations and may be configured or arranged in a certain manner. In example embodiments, one or more computer systems (e.g., a standalone, client or server computer system) or one or more processors may be configured by software (e.g., an application or application portion) as a hardware-implemented module that operates to perform certain operations as described herein.

In various embodiments, a hardware-implemented module may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a processor or other programmable device) that is temporarily configured by software to perform certain operations. Accordingly, the term "hardware-implemented module" should be understood to encompass a tangible entity, be that an entity that is physically constructed, permanently configured (e.g., hardwired) or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules may provide information to, and receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connects the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and store the output of that operation in a memory device to which it is communicatively coupled. A further hardware-implemented module may then, at a later time, access the memory device to retrieve and process the stored output. Hardware-implemented modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but also deployed across a number of machines. In some example embodiments, the processor or processors may be located in a single location, while in other embodiments the processors may be distributed across a number of locations.

The one or more processors may also operate to support performance of the relevant operations in a "cloud computing" environment or as a "software-as-a-service" (SaaS) service. For example, at least some of the operations may be performed by a group of computers (as examples of machines including processors), with these operations being accessible via a network (e.g., the Internet) and via one or more appropriate interfaces (e.g., Application Program Interfaces (APIs)).

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a non-transitory machine-readable medium, for execution by, or to control the operation of, data processing apparatus, e.g., a programmable processor, a computer, or multiple computers.

A computer program may be written in any form of programming language, including compiled or interpreted languages, and it may be deployed in any form, including as a stand-alone program or as a module, subroutine, or other unit suitable for use in a computing environment. A computer program may be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations may also be performed by, and apparatus of example embodiments may be implemented as, special purpose logic circuitry, e.g., FPGAs or ASICs.

The computing system may include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Figure 12:
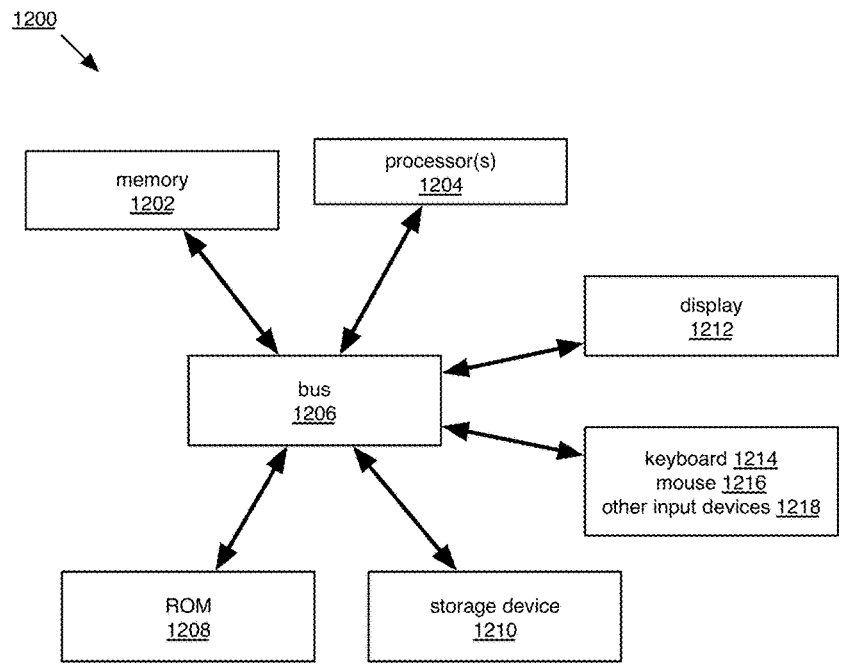
FIG. 12 is a block diagram showing an exemplary computing device, consistent with some embodiments of the invention.

FIG. 12 is a block diagram showing an exemplary computing system 1200 that is representative any of the computer systems or electronic devices discussed herein. Note, not all of the various computer systems have all of the features of system 1200. For example, systems may not include a display inasmuch as the display function may be provided by a client computer communicatively coupled to the computer system or a display function may be unnecessary.

System 1200 includes a bus 1206 or other communication mechanism for communicating information, and a processor 1204 coupled with the bus 1206 for processing information. Computer system 1200 also includes a main memory 1202, such as a random access memory or other dynamic storage device, coupled to the bus 1206 for storing information and instructions to be executed by processor 1204. Main memory 1202 also may be used for storing temporary variables or other intermediate information during execution of instructions to be executed by processor 1204.

System 1200 includes a read only memory 1208 or other static storage device coupled to the bus 1206 for storing static information and instructions for the processor 1204. A storage device 1210, which may be one or more of a hard disk, flash memory-based storage medium, magnetic tape or other magnetic storage medium, a compact disc (CD)-ROM, a digital versatile disk (DVD)-ROM, or other optical storage medium, or any other storage medium from which processor 1204 can read, is provided and coupled to the bus 1206 for storing information and instructions (e.g., operating systems, applications programs and the like).

Computer system 1200 may be coupled via the bus 1206 to a display 1212 for displaying information to a computer user. An input device such as keyboard 1214, mouse 1216, or other input devices 1218 may be coupled to the bus 1206 for communicating information and command selections to the processor 1204.

The processes referred to herein may be implemented by processor 1204 executing appropriate sequences of computer-readable instructions contained in main memory 1204. Such instructions may be read into main memory 1204 from another computer-readable medium, such as storage device 1210, and execution of the sequences of instructions contained in the main memory 1204 causes the processor 1204 to perform the associated actions. In alternative embodiments, hard-wired circuitry or firmware-controlled processing units (e.g., field programmable gate arrays) may be used in place of or in combination with processor 1204 and its associated computer software instructions to implement the invention. The computer-readable instructions may be rendered in any computer language including, without limitation, Objective C, C#, C/C++, Java, assembly language, markup languages (e.g., HTML, XML), and the like. In general, all of the aforementioned terms are meant to encompass any series of logical steps performed in a sequence to accomplish a given purpose, which is the hallmark of any computer-executable application. Unless specifically stated otherwise, it should be appreciated that throughout the description of the present invention, use of terms such as "processing", "computing", "calculating", "determining", "displaying", "receiving", "transmitting" or the like, refer to the action and processes of an appropriately programmed computer system, such as computer system 1200 or similar electronic computing device, that manipulates and transforms data represented as physical (electronic) quantities within its registers and memories into other data similarly represented as physical quantities within its memories or registers or other such information storage, transmission or display devices.

Figure 13:
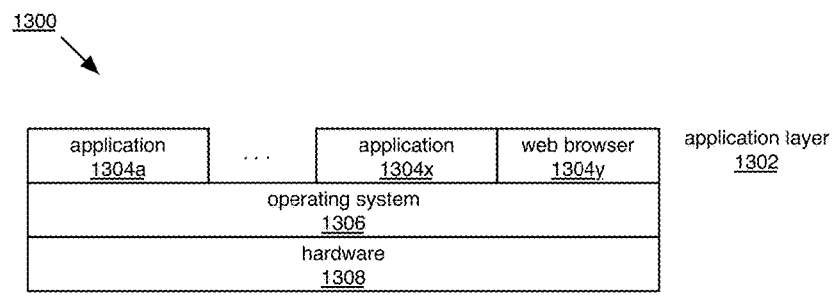
FIG. 13 is a block diagram showing an exemplary computing system, consistent with some embodiments of the invention.

FIG. 13 illustrates a computer system 1300 from the point of view of its software architecture. Computer system 1300 may be any of the electronic devices or, with appropriate applications comprising a software application layer 1302, may be a computer system for use with the publishing tools described herein. The various hardware components of computer system 1300 are represented as a hardware layer 1308. An operating system 1306 abstracts the hardware layer and acts as a host for various applications 1304, that run on computer system 1300. The operating system may host a web browser application 1304y, which may provide access for the user interfaces, etc.

Figure 14:
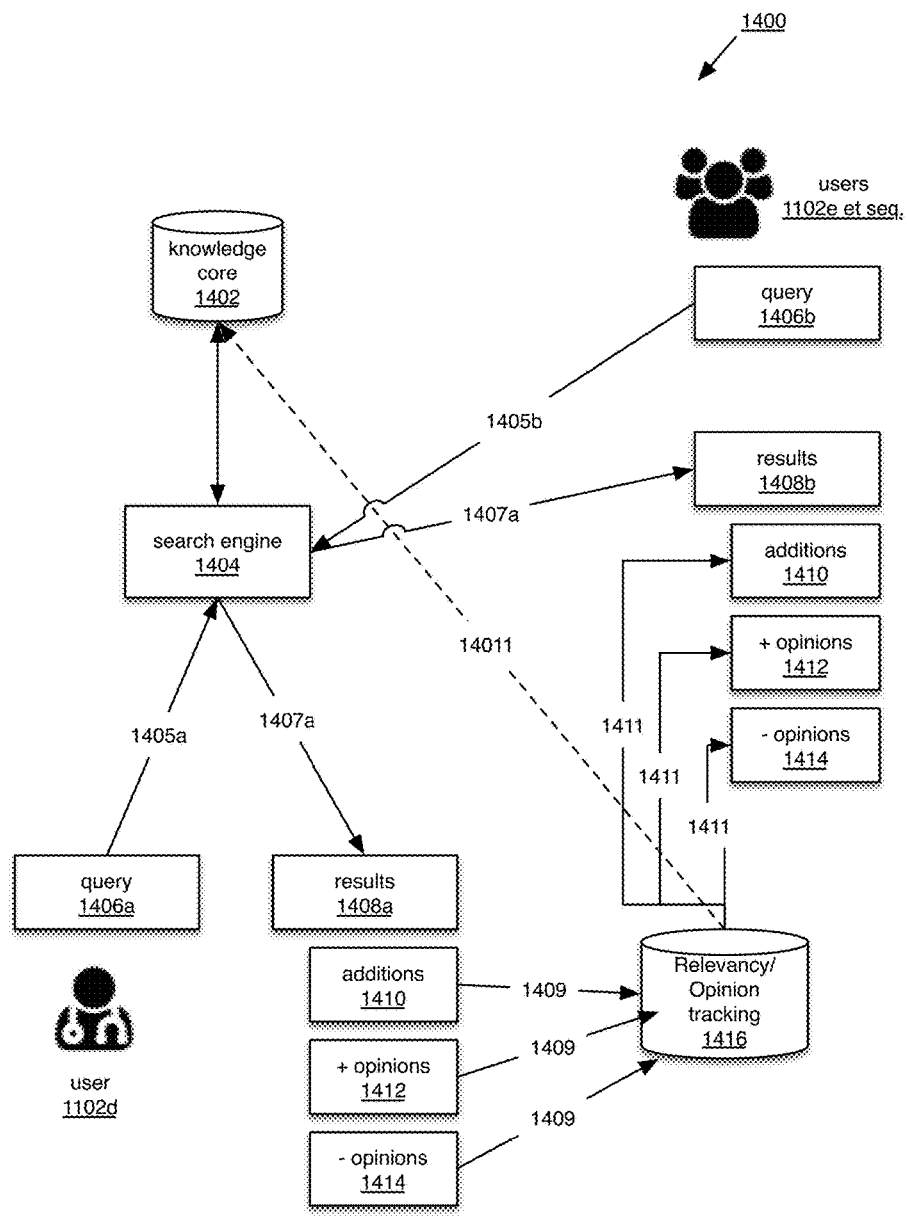
FIG. 14 is a diagram showing an exemplary system for inferring and delivering precision medicine information, in accordance with some embodiments of the invention.

FIG. 14 is a diagram showing an exemplary system 1400 for inferring and delivering precision medicine information. In certain embodiments, the knowledgebase is enhanced through active use by users, particularly users with domain-specific expertise or knowledge such as medical practitioners or medical researchers. The system may enable collaboration by incorporating annotations from such users, which in turn may affect search results seen in response to later queries. By enabling collaboration across groups of users, the knowledgebase becomes more accurate and complete. Further, accuracy may be enhanced by associating annotations with authorship information. Peer review of the annotations and authorship information may inform whether to ignore, delete, or formalize an annotation as trusted information. This approach of integrating collaborative annotation of the knowledgebase is novel in this context.

A user can annotate a specific result (e.g., a specific drug pertaining to a mutation and diagnosis) with an affirmative or negative opinion that may be shared by or with subsequent recipients of a similar search. In certain embodiments, a user may augment a search to include additional results (e.g., a specific drug that applies to a diagnosis and mutation that was previously missing from the search results). Such an augmented result may be shared such that subsequent users may see the result included in the results for a similar search, and in certain embodiments subsequent users would see an annotation describing the user who provided the result and the reason for including it (e.g., user's name and institution). A reason may include a citation to a publication. In certain embodiments, such annotations may be exposed as a shared annotation to everyone. In certain embodiments, such annotations may be exposed only to a particular organization or group affiliated with the annotating user (e.g., a diagnostic lab, a hospital, or an academic institution).

In one example, a user such as user 1102d may submit a query 1406a to a search engine 1404 in system 1400 (1405a). User 1102d may be a subject matter expert, such as an oncologist with expertise in the etiology of cancers. For example, user 1102d may perform a search for a diagnosis and variant. Search engine 1404 obtains results from knowledge core 1402. In certain embodiments, knowledge core 1402 may be a component of knowledgebase 108. In certain embodiments, knowledge core 1402 may be knowledgebase 108. Results 1408a are provided to user 1102d (1407a). The user may add an additional drug that should exist in the result set (e.g., 1410). The user also comments positively on certain results (1412) and negatively on other results (1414) in results 1408a. Such comments, or annotations, may be considered opinions. Those annotations (e.g., 1412 and 1414) and additions (e.g., 1410) may be stored for subsequent similar queries (1409).

Relevancy/opinion tracking 1416 may be a component of knowledgebase 108 and/or knowledge core 1402. In certain embodiments, relevancy annotations and opinion annotations may be selectively adopted into the knowledgebase 108, which will influence the scoring algorithm pertaining to results generation. In certain embodiments, annotations are reviewed by users 1102 in general, or by specific individuals, before being integrated into knowledgebase 108.

A subsequent query 1406b may be submitted by additional users 1102e et seq (1405b). User 1102e may be affiliated with user 1102d (e.g., the two users are members of the same organization, such as a research institution or medical group). (In certain embodiments, user 1102e is unaffiliated with user 1102d—e.g., not members of the same organization.) In certain embodiments, if the two users are affiliated, the additions 1410 and annotations 1412 and 1414 are automatically added to the results 1408b that are provided to user 1102e (1411). In certain embodiments, if user 1102d is affiliated with a private organization, the results 1408b are not augmented with the additions 1410 and annotations 1412 and 1414.

The foregoing description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," and the like are used merely as labels, and are not intended to impose numerical requirements on their objects.

What is claimed is:

1. A method comprising:
automatically connecting, in a knowledgebase repository, a plurality of database domain instances by examining relationships between the database domain instances, wherein the database domain instances belong to one or more domains, the domains including patient conditions, clinical findings, genes and gene mutations associated with the patient conditions, drugs associated with treatment of the patient conditions, clinical trials regarding the drugs, and members of drug classes within which the drugs exist, wherein the connections between the database domain instances include (i) at least a positive relationship between a first database domain instance and a second database domain instance, the first database domain instance and the second database domain instance belonging to different domains, (ii) at least a negative relationship that serves as an exclusion factor between a third database domain instance and a fourth database domain instance, the third database domain instance and the fourth database domain instance belonging to different domains, (iii) at least a parent-child relationship between a fifth database domain instance and a sixth database domain instance, the fifth database domain instance and the sixth database domain instance belonging to the same domain, and (iv) at least a synonymous relationship between a seventh database domain instance and an eighth database domain instance, the seventh database domain instance and the eighth database domain instance belonging to the same domain;

receiving a plurality of query domain instances concerning a medical condition and a status of a patient;

determining a candidate list of database domain instances, the candidate list including a subset of the database domain instances representing drugs and trials that are connected to the plurality of query domain instances and not excluded by the exclusion factor;

ranking the candidate list of database domain instances using a confidence measure for each database domain instance developed according to strengths of the connections between the plurality of database domain instances;

facilitating a display of the candidate list of database domain instances and each respective confidence measure;

receiving, from a user, a data domain instance to augment the candidate list of database domain instances; and in response to receiving the data domain instance to augment the candidate list of database domain instances, forming a new connection in the knowledgebase repository between at least two of the data domain instances.

2. The method of claim 1, further comprising:
prior to facilitating the display of the candidate list of database domain instances, removing database domain instances from the candidate list if the respective confidence measure is below a threshold.

3. The method of claim 1, wherein the exclusion factor excludes database domain instances representing trials that are associated with a trial location that is more distant than a maximum distance from a location of the patient.

4. The method of claim 1, wherein the plurality of database domain instances are additionally connected using manual annotation.

5. The method of claim 1, wherein the plurality of query domain instances includes a condition and a drug and the confidence measure of the drug incorporates a Food and Drug Administration (FDA) approval status of the drug for treatment of the condition.

6. The method of claim 1, wherein the relationships comprise organization-subsidiary relationships.

7. The method of claim 1, wherein the relationships comprise: domains concerning the same signaling pathway, domains concerning the same molecular scaffold, domains concerning the same gene, and domains concerning the same mutation.

8. The method of claim 1, wherein the query domain instances concern a type of cancer, and the candidate list of database domain instances includes one or more database domain instances representing drugs for treating the type of cancer.

9. The method of claim 1, further comprising providing suggested query domain instances for approval based on frequently observed combinations of past query domain instances.

10. The method of claim 1, wherein the step of receiving the plurality of query domain instances comprises:
facilitating a display of one or more questions;
receiving one or more query domain instances responsive to the one or more questions; and
providing a description of a query based on the received one or more query domain instances, wherein the description includes applicable AND and OR operations.

11. The method of claim 1, further comprising providing a mechanism to request enrollment in a trial, wherein the candidate list includes the trial and a status of the trial is recruiting.

12. A system comprising one or more memories and one or more processors, the one or more memories storing instructions that, when executed by the one or more processors, cause the one or more processors to:
automatically connect, in a knowledgebase repository, a plurality of database domain instances by examining relationships between the database domain instances, wherein the database domain instances belong to one or more domains, the domains including patient conditions, clinical findings, genes and gene mutations associated with the patient conditions, drugs associated with treatment of the patient conditions, clinical trials regarding the drugs, and members of drug classes within which the drugs exist, wherein the connections between the database domain instances include (i) at least a positive relationship between a first database domain instance and a second database domain instance, the first database domain instance and the second database domain instance belonging to different domains, (ii) at least a negative relationship that serves as an exclusion factor between a third database domain instance and a fourth database domain instance, the third database domain instance and the fourth database domain instance belonging to different domains, (iii) at least a parent-child relationship between a fifth database domain instance and a sixth database domain instance, the fifth database domain instance and the sixth database domain instance belonging to the same domain, and (iv) at least a synonymous relationship between a seventh database domain instance and an eighth database domain instance, the seventh database domain instance and the eighth database domain instance belonging to the same domain;

receive a plurality of query domain instances concerning a medical condition and a status of a patient;

determine a candidate list of database domain instances, the candidate list including a subset of the database domain instances representing drugs and trials that are connected to the plurality of query domain instances and not excluded by the exclusion factor;

rank the candidate list of database domain instances using a confidence measure for each database domain instance developed according to strengths of the connections between the plurality of database domain instances; and facilitate a display of the candidate list of database domain instances and each respective confidence measure;

receive, from a user, a data domain instance to augment the candidate list of database domain instances; and in response to receiving the data domain instance to augment the candidate list of database domain instances, form a new connection in the knowledgebase repository between at least two of the data domain instances.

13. The system of claim 12, further comprising instructions that cause the one or more processors to:

prior to facilitating the display of the candidate list of database domain instances, remove database domain instances from the candidate list if the respective confidence measure is below a threshold.

14. The system of claim 12, wherein the exclusion factor excludes database domain instances representing trials that are associated with a trial location that is more distant than a maximum distance from a location of the patient.

15. The system of claim 12, wherein the plurality of database domain instances are additionally connected using manual annotation.

16. The system of claim 12, wherein the plurality of query domain instances includes a condition and a drug and the confidence measure of the drug incorporates a Food and Drug Administration (FDA) approval status of the drug for treatment of the condition.

17. The system of claim 12, wherein the relationships comprise organization-subsidiary relationships.

18. The system of claim 12, wherein the relationships comprise: domains concerning the same signaling pathway, domains concerning the same molecular scaffold, domains concerning the same gene, and domains concerning the same mutation.

19. The system of claim 12, wherein the query domain instances concern a type of cancer, and the candidate list of database domain instances includes one or more database domain instances representing drugs for treating the type of cancer.

20. The system of claim 12, further comprising providing suggested query domain instances for approval based on frequently observed combinations of past query domain instances.

* * * * *